United States Patent [19]
Chin et al.

[11] Patent Number: 5,336,237
[45] Date of Patent: Aug. 9, 1994

[54] REMOVAL OF TISSUE FROM WITHIN A BODY CAVITY

[75] Inventors: Albert K. Chin, Palo Alto; John McIntyre, San Carlos; Stephen A. Morse, Palo Alto, all of Calif.

[73] Assignee: Devices for Vascular Intervention, Inc., Redwood City, Calif.

[21] Appl. No.: 111,984

[22] Filed: Aug. 25, 1993

[51] Int. Cl.⁵ .............................................. A61B 17/32
[52] U.S. Cl. ...................................... 606/167; 604/22; 604/164; 604/27; 604/28; 606/185
[58] Field of Search .......................... 604/22, 27, 28; 606/108, 114, 115, 167, 185, 186

[56] References Cited
U.S. PATENT DOCUMENTS

| | | | |
|---|---|---|---|
| 5,215,521 | 6/1993 | Cochran et al. | 604/22 |
| 5,224,930 | 7/1993 | Spaeth et al. | 604/33 |
| 5,226,429 | 7/1993 | Kuzmak | 606/157 |

*Primary Examiner*—Jerome L. Kruter
*Attorney, Agent, or Firm*—Crosby, Heafey, Roach & May

[57] ABSTRACT

A method and system for removing an organ or piece of tissue severed from its supporting tissue within a patient's body cavity, such as the abdominal cavity, which includes an elongated expandable tubular member with a sealed interior. In one preferred embodiment for morcellation, means are provided within the sealed interior to tear or cut off tissue fragments from the organ or tissue which are small enough to pass out of the patient's body cavity through an inner lumen of an exit trocar sheath disposed within the patient and in communication with the body cavity. The organ or piece of tissue is placed within an inner lumen defined by the sealed interior through an opening provided in a leading portion of the elongated expandable tubular member. The organ or piece of tissue is fragmented into smaller pieces which are withdrawn from the patient's body cavity by the passage of the morcellation system through the inner lumen of the exit trocar sheath. In one embodiment of the morcellation system, one or more elongated cutting strips are disposed within the inner lumen defined by the sealed interior and secured to the lining to cut or tear the tissue into small fragments. In another embodiment of the invention one or more elongated helical ribbons are provided to cut or tear the tissue into small fragments.

22 Claims, 4 Drawing Sheets

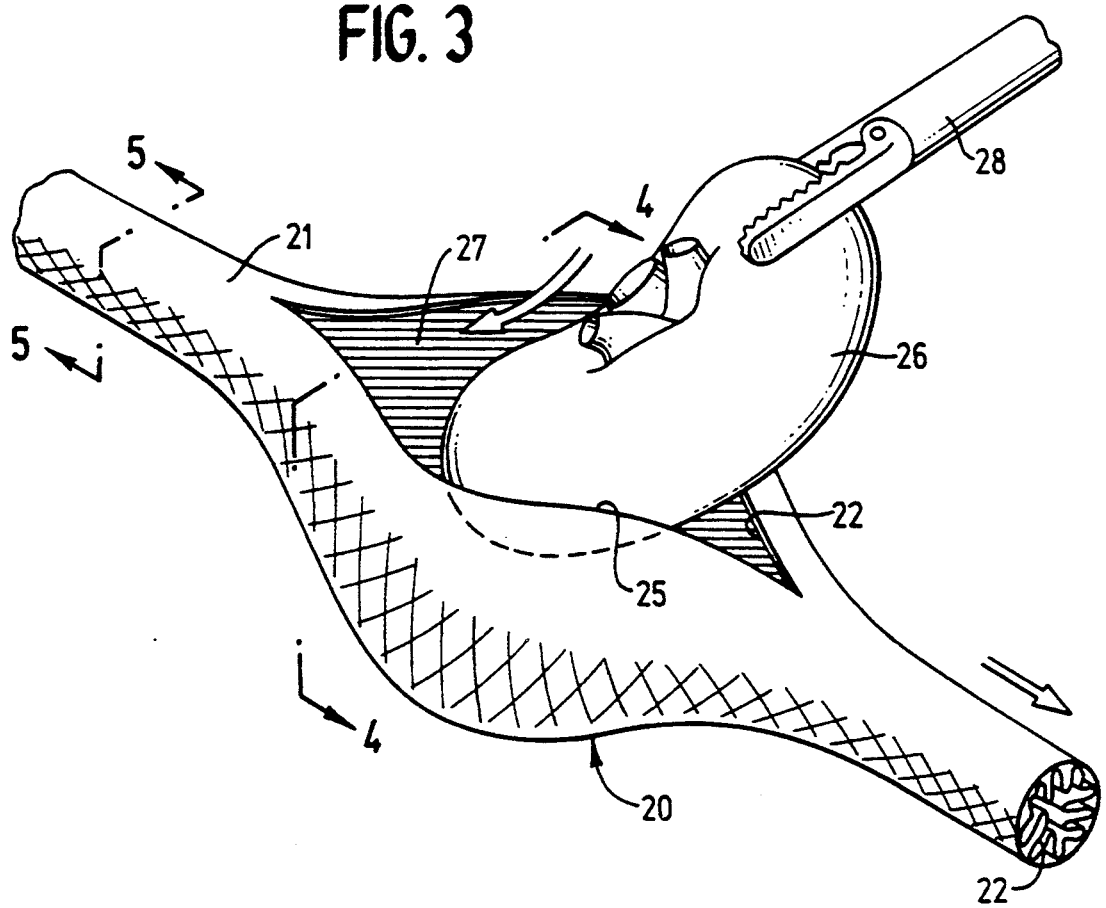
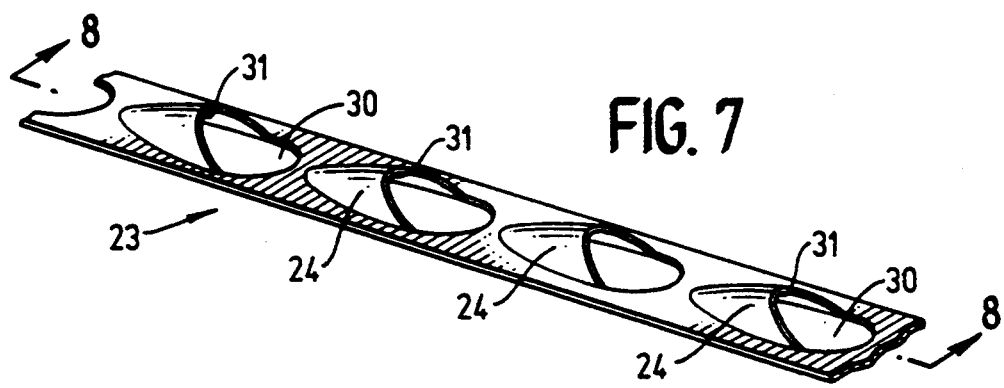
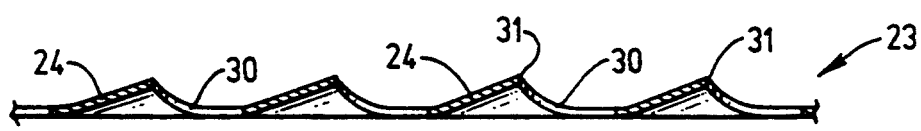

REMOVAL OF TISSUE FROM WITHIN A BODY CAVITY

FIELD OF THE INVENTION

This invention relates to an intracorporeal method and system for morcellating an organ or other piece of tissue within a patient's body cavity.

BACKGROUND OF THE INVENTION

Laparoscopic surgery is now a widely practiced procedure for operating on a patient's ovaries, uterus, gall bladder, bowels, appendix and the like. This surgery involves making small incisions through a patient's abdominal wall by means of trocars and passing laparoscopes and surgical instruments through the trocar sheaths left in place in the abdominal wall to perform the desired surgical procedure. Typically, a trocar of about 12 mm dia. is employed to make an incision through the patient's navel, and the trocar sheath left in place through the abdominal wall is used for laparoscopic viewing of the surgical field within the patient's abdominal cavity. Other trocar incisions are made at various locations in the patient's abdominal wall so that surgical instruments and tubes for introducing irrigation fluid into and aspirating fluids from the abdominal cavity can be advanced into and removed from the abdominal cavity through the other trocar sheaths disposed through the abdominal wall. All of the trocar sheaths are usually oriented toward the surgical field within the abdominal cavity.

The laparoscopic surgical removal of large pieces of tissue, particularly a large organ such as kidney, a uterus, a liver and the like has posed a formidable problem, because such organs are too large to be withdrawn through conventional trocar sheaths. If the organ is cut into small enough pieces within the abdominal cavity to be withdrawn through a trocar sheath, there is a high probability that tissue debris will be left within the abdominal cavity at the end of the procedure which can lead to development of septic conditions within the abdominal cavity, e.g. peritonitis, and other problems after the trocar sheaths have been removed and the incisions closed. Additionally, cutting a large organ or piece of tissue into smaller pieces and withdrawing the individual severed pieces of tissue lengthen and complicate the surgical procedure and as a result many of the advantages of endoscopic surgical procedures may be lost.

U.S. Pat. Nos. 5,037,379 and 5,215,521 describe a method and system for the morcellation of an organ, such as kidney, within a patient's body cavity by placing the severed organ into a plastic bag or container within the patient's body cavity and then inserting a cutting means into the bag to cut up the organ into smaller fragments to facilitate passage of the bag and its contents through the trocar sheath or the incision. However, the systems disclosed in these references have some difficulty in maintaining contact between the tissue to be morcellated and the cutting means and in avoiding contact between the cutting means and the bag or container holding the organ.

What has been needed and heretofore unavailable is a method and system for morcellating an organ or other piece of tissue within the patient's body cavity which maintains contact between cutting means and the organ to be morcellated while avoiding damaging contact between the cutting means and the container holding the organ. The present invention satisfies these and other needs.

SUMMARY OF THE INVENTION

This invention is directed to a method and system for removing an organ or a piece of tissue from within a patient's body cavity and particularly to the endoscopic surgical procedures for such use.

The system for removing an organ or a piece of tissue include an elongated expandable tubular member with a sealed interior, e.g. an impervious lining defining an inner lumen within at least a portion of the elongated expandable tubular member. The elongated expandable tubular member has leading and trailing portions and an opening is provided in the leading portion to facilitate insertion of the organ or piece of tissue into the expanded inner lumen thereof. In some instances the organ or tissue can be compressed or fragmented sufficiently by advancement of the elongated expandable tubular member into and through a trocar sheath. However, usually means are disposed within the inner lumen to cut or tear tissue into small fragments and may be secured to the impervious lining.

In operation, the patient is first prepped for endoscopic surgery, e.g. laparoscopic nephrectomy, with a plurality of trocar sheaths placed through a wall defining the patient's body cavity, e.g. the abdominal cavity. The body cavity is expanded by filling with a suitable gas, such as $CO_2$, to facilitate the subsequent endoscopic surgery. The organ to be removed is first severed from its surrounding supporting tissue and then the leading portion of the elongated expandable tubular member of the invention, as described above with an impervious lining and tissue cutting means, is advanced into the interior of the patient's body cavity through an inner lumen of an in-place entry trocar sheath and then it is directed out of the patient's body cavity through an inner lumen of an in-place exit trocar sheath. The opening in the leading portion of the elongated expandable tubular member, which is adapted to receive the tissue to be morcellated, may be formed in the part of the leading portion remaining within the interior of the body cavity prior to the insertion thereof into the patient or it may be formed insitu by the physician by cutting an opening with a scalpel or other cutting device advanced through a trocar sheath. The opening is expanded to facilitate insertion of an organ or piece of tissue by pressing inwardly on one or both portions of the expandable tubular member extending out of the entry and exit trocar sheaths. The severed organ or tissue within the body cavity is positioned by suitable laparoscopic forceps or other grasping means through the expanded opening into the inner lumen of the elongated expandable tubular member. Alternatively, the organ or piece of tissue may be introduced into an opening in the leading end of the elongated tubular member before the leading portion is advanced through the exit trocar sheath.

Once the organ or piece of tissue is disposed within interior of the impervious lining, tension is applied to the portion of the elongated expandable tubular member which extends out of the exit trocar sheath, pulling the tissue removal means through the inner lumen of the in-place exit trocar sheath. The organ or piece of tissue disposed within the impervious lining will usually be too large, be inappropriately shaped or be too inelastic to be able to readily pass through the lumen of the exit trocar sheath along with the tissue removal means. However, by providing tissue cutting or tearing means within the interior of the tissue removal means, when the tissue removal means is advanced through the inner lumen of the in-place exit trocar sheath, the cutting or tearing means will make contact with the organ or piece of tissue, removing fragments which are small enough to pass along with the tissue removal means through the inner lumen of the in-place exit trocar sheath. The organ or piece of tissue to be comminuted into small fragment remains in the inner lumen of the tissue removal means within the body cavity while the tissue removal means passes through the exit trocar sheath. The morcellation system must be long enough so that the organ or piece of tissue is sufficiently debulked to be small enough to pass through the exit trocar sheath before the proximal end of the morcellation means passes through.

In one presently preferred embodiment of the invention, the elongated cutting or tearing means is one or more elongated strips which have a plurality of raised teeth adapted to tear or cut off fragments of the organ or tissue within the inner lumen of the sealed inner lumen. Three of such cutter strips are secured by a suitable adhesive or other means to the inner surface of the impervious lining and are moved therewith.

In another presently preferred embodiment the cutting means is a helical ribbon with an exterior cutting surface and an inner surface secured to a flexible wire or cable element by suitable means such as solder or an adhesive. Three of such cutting means can be employed within the interior of the morcellation means to cut or tear off fragments of tissue. In this embodiment the cutting element is not secured to the lining.

The present invention may be used to readily remove a variety of organs and pieces of tissue from a patient's body cavity. The organ or piece of tissue to be removed is isolated within the impervious interior of the expandable tubular member so there is little or no risk of leaving pieces of tissue within the body cavity at the end of the procedure. These and other advantages of the invention will become more apparent from the following detailed description of the invention when taken in conjunction with the attached exemplary drawings.

BRIEF DESCRIPTION OF THE DRAWINGS

FIG. 3 is a perspective view of the leading portion of the tissue removal system shown in FIG. 2 with the outer tubular member expanded to expand the opening therein and facilitate insertion of a severed kidney.

FIG. 7 is a partial perspective view of a presently preferred cutting member.

FIG. 8 is longitudinal cross-sectional view taken along the lines 8—8 shown in FIG. 7.

DETAILED DESCRIPTION OF THE INVENTION

Figure 1:
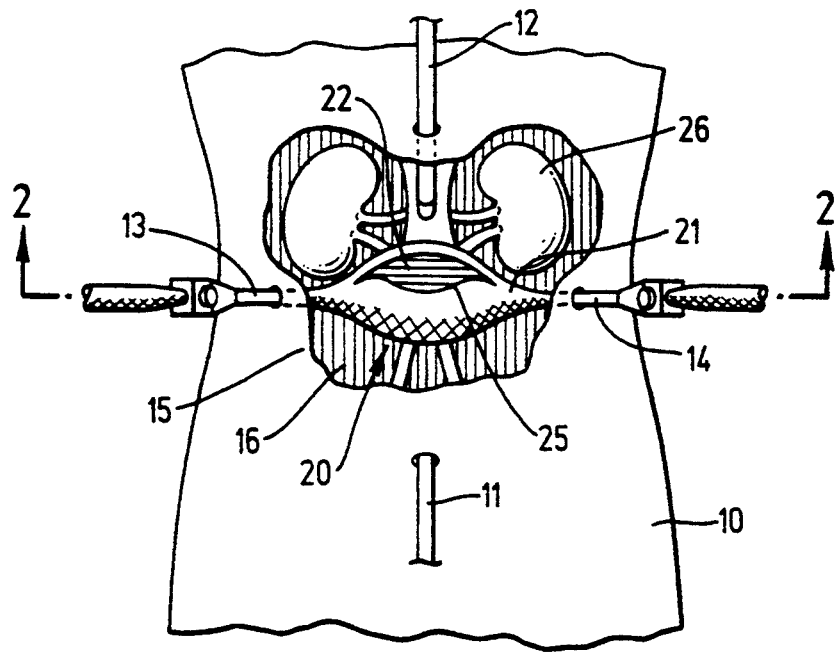
FIG. 1 is plan view of the anterior side of a patient's torso indicting the placements of trocar sheaths for the laparoscopic removal of a patient's kidney.
Figure 2:
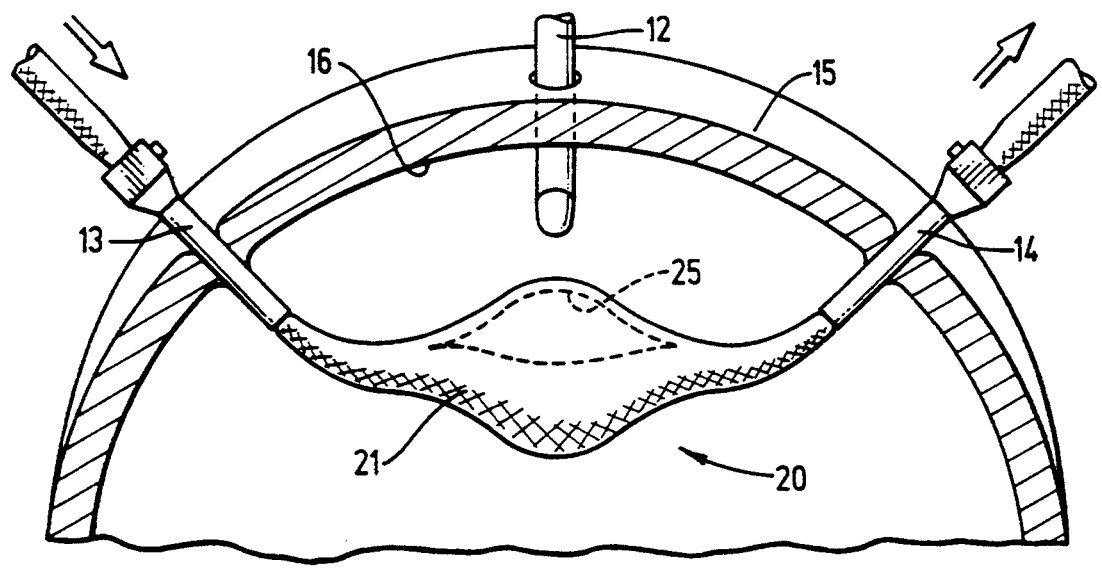
FIG. 2 is a schematic transverse cross-sectional view of a patient in a horizontal plane taken along the lines 2—2 shown in FIG. 1 with the tissue removal system of the invention disposed within the patient's abdominal cavity and extending through entry and exit trocar sheaths.

FIG. 1 schematically illustrates the torso 10 of a patient prepped for a laparoscopic procedure with a plurality of trocar sheaths 11, 12, 13 and 14 in-place through the patient's abdominal wall 15 providing access to the patient's abdominal cavity 16 shown in FIG. 2. A laparoscope (not shown) will be disposed within the lumen of trocar sheath 11 to facilitate observation of the operation within the abdominal cavity 16. Trocar sheath 12 is used to pass instruments and aspiration and irrigation tubes into the abdominal cavity 16 to perform the surgical procedure. Trocar sheaths 13 and 14 are used to pass the morcellation means 20, as shown in FIG. 2, into and out of the patient's abdominal cavity 16.

Figure 4:
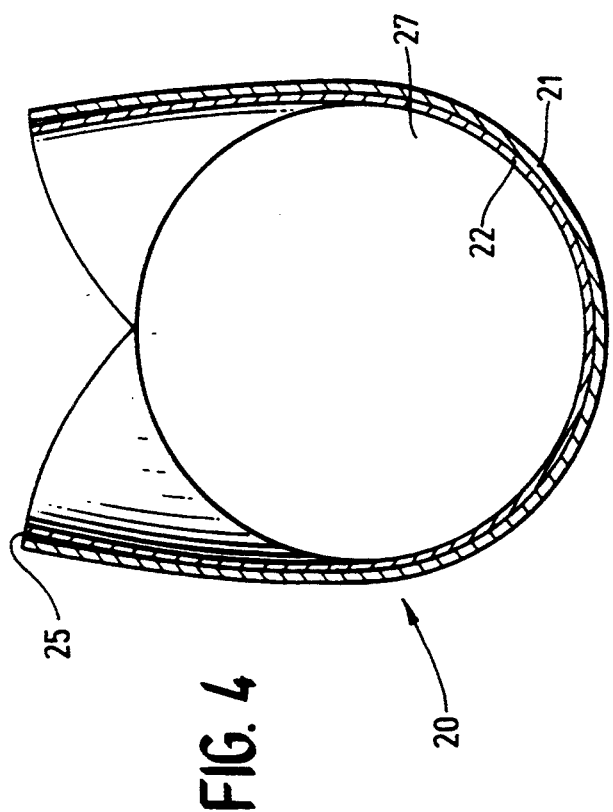
FIG. 4 is a transverse cross-sectional view of the tissue removal system shown in FIG. 3 taken along the lines 4—4.

The morcellation means 20 of the invention and the various components thereof, are shown in FIGS. 1–8. As indicated, the morcellation means generally includes an expandable tubular member 21, an impervious inner lining 22 and a plurality of cutting strips 23 which have raised teeth 24 for tearing or cutting tissue. As shown in FIGS. 3 and 4, the leading portion of the outer tubular member 21 has an opening 25 which is expanded, as shown, to facilitate the insertion of a kidney 26 into the inner lumen 27 of the outer tubular member defined by the impervious lining 22 by the manipulation of the laparoscopic forceps or grasping means 28. The impervious lining 22 may be secured to the interior of the expandable tubular member 21 around the edge of the opening 25 to ensure that the kidney 26 is disposed within the inner lumen 27 of the impervious lining rather than between the lining and the outer tubular member. As depicted in the transverse cross-sectional view in FIG. 5, at locations proximal to the opening 25, the impervious inner lining is disposed within the interior of the outer tubular member but need not be secured thereto. The impervious lining 22 is preferably formed of a relatively inelastic plastic material which when expanded from its folded condition has an outer diameter approximately the same size as the expanded inner diameter of the outer tubular member 21.

Figure 5:
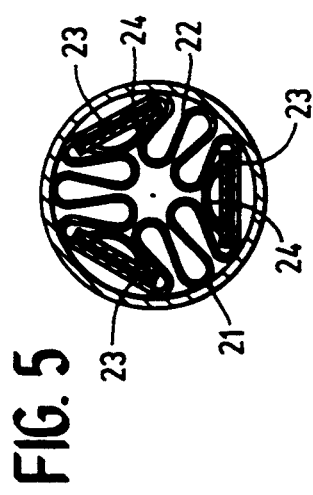
FIG. 5 is a transverse cross-sectional view of the tissue removal system shown in FIG. 3 taken along the lines 5—5.
Figure 6:
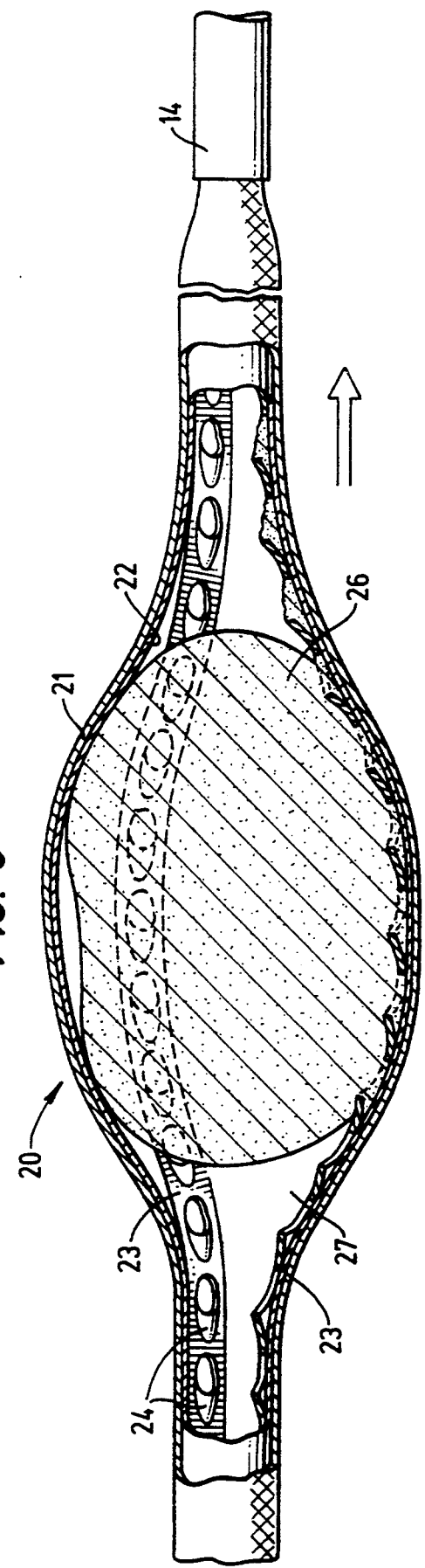
FIG. 6 is an elevational view partially in section of a morcellation means at the entry of the exit trocar sheath illustrating the morcellation of an organ within the interior or the morcellation means.

In the embodiment shown in the FIG. 5, three tissue cutting strips 23 are secured by suitable means such as an adhesive to the impervious lining 22 at locations proximal to the opening 25. The tissue cutting strips 23, as shown in FIGS. 6 and 7 have a plurality of teeth 24 which may be conveniently formed by punching a circular hole 30 in a metallic strip, e.g. stainless steel, and press forming the portion of the strip defining the trailing edge 31 of the circular hole outwardly to form the raised tooth 24. The trailing edge 31 may be sharpened by conventional means, if needed.

The operation of the morcellation system 20 after the insertion of the kidney 25 into the inner lumen 27 defined by the impervious inner layer 22 is best depicted in FIG. 6. The outer tubular member 21, the impervious liner 22 and the cutting strips 23 are pulled through the exit trocar sheath 14. As the cutting strips 23 move over and in contact with the organ 25, which remains within the inner lumen in the body cavity, the teeth 24 on the cutting strips tear or cut off fragments of tissue which are small enough to pass through the inner lumen of the exit trocar sheath 14 along with the morcellation means. The kidney 25 is initially too large to pass through the inner lumen of the exit trocar sheath 14 along with the morcellation means 20, but its size is gradually reduced as fragments of tissue are torn or cut off by the passage of the cutting strips 23 until the remnant of the kidney is sufficiently small to pass through the exit trocar 14 within the morcellation means. Fluid may be provided within the inner lumen 27 to facilitate transfer of tissue fragments. The impervious inner layer 22 may be provided with a lubricous surface to facilitate relative movement between the kidney 26 and the morcellation means 20.

The expandable tubular member 21 is preferably formed of braided plastic strands such as polyethylene. For the removal of kidneys and other similarly large organs, the unexpanded diameter is about one inch and the expanded diameter is about three inches. Expansion of a section of the expandable tubular member 21 such as that portion surrounding the opening 25 is effected by applying a longitudinal compressive force, e.g. pushing portions of the tubular member inwardly on both sides of the section to be expanded. The length and other dimensions of the opening are selected to facilitate the insertion of the kidney 26 into the inner lumen 27. Other dimensions for the tubular member 21 may be more appropriate for other organs or tissue of different sizes.

The impervious lining 22 is a thin walled tubular member formed of a suitable relatively inelastic plastic material, such as polyethylene which is quite strong and exhibits good lubricity when wet.

The cutting strip 23 may be formed of a variety of relatively strong materials including metals and plastic, but stainless steel is presently preferred.

The overall length of the morcellation means 20 may range from about 3 to about 20 feet depending upon the size and the nature of the organ or tissue to be removed. There is no need to extend the length of the morcellation means beyond that needed to reduce the organ to a size which permits passage through the inner lumen of the exit trocar sheath 14. Typical lengths are about 5 to 15 feet.

Figure 9:
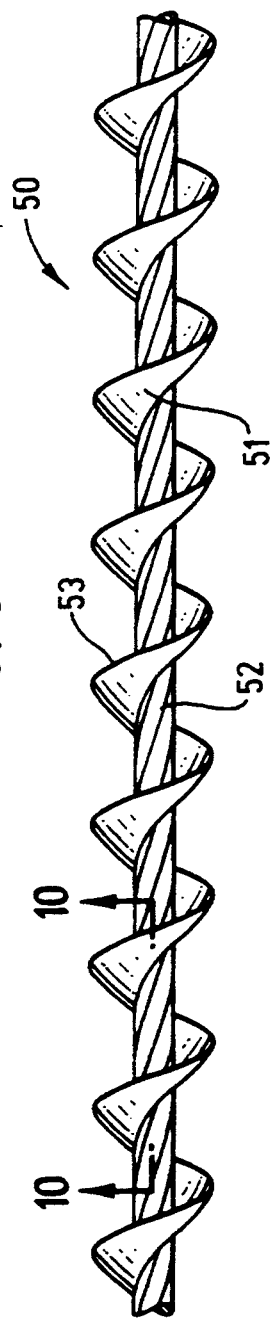
FIG. 9 is an elevational view of another presently preferred cutting member.
Figure 11:
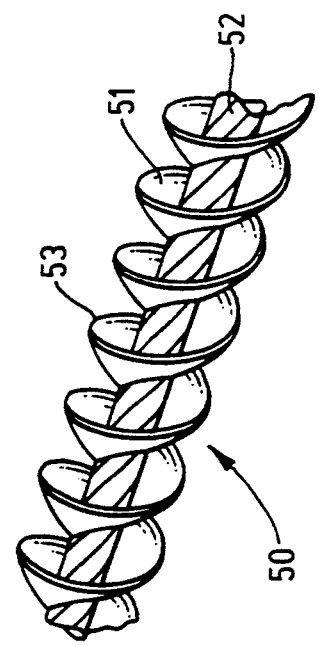
FIG. 11 is a partial perspective view of the cutting member shown in FIG. 9.
Figure 10:
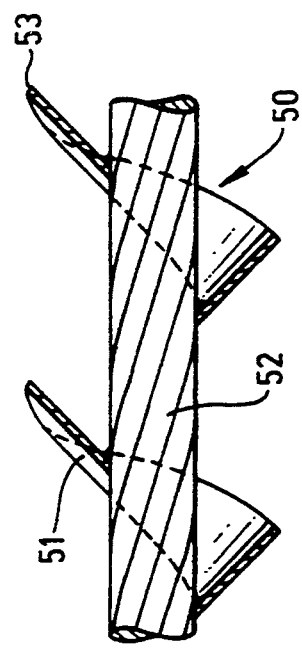
FIG. 10 is an enlarged partial cross-sectional view of the cutting member shown in FIG. 9 taken along the lines 10—10.

Another presently preferred cutting or tearing member 50 is depicted in FIGS. 9–11 which includes a helical ribbon 51 secured by soldering or a suitable adhesive to supporting core member 52. The exterior edge 53 of the helical ribbon 51 is sufficiently sharp to cut or tear fragments of tissue from an organ or other piece of tissue. The cutting or tearing member 50 need not be secured to the interior of the elongated expandable tubular member of the morcellation system. It is otherwise used in essentially the same manner as the previously discussed embodiment shown in FIGS. 1, 2, 3, 4 and 6.

While the present invention has been described herein primarily in terms of certain preferred embodiments, such as those suitable for morcellating a kidney, it should be recognized that the invention can be employed to the removal of a variety of organs and tissue from a patient's body cavity or lumen. Additionally, modifications can be made to the described embodiments, e.g. the outer expandable tubular member need not be braided or woven plastic strands but may be formed of tough elastomeric film or fine metallic wire or ribbon (e.g. pseudoelastic NiTi alloys). Likewise, the impervious lining need not be inelastic but may be elastically expandable. The expandable tubular member need not have a separate impervious lining as described in the preferred embodiment but may be merely sealed so as to prevent the loss of interior contents into the body cavity. Moreover, as recognized by those skilled in the art, other modifications and improvements can be made to the invention without departing from the scope thereof.

What is claimed is:

1. A system for removing an organ or other piece of tissue from within a patient's body cavity or lumen including:
    a) first and second trocar sheaths configured to be inserted into a patient's body cavity or lumen and having inner lumens in communication with the body cavity or lumen; and
    b) a tissue removing means which is configured to be advanced through the inner lumen of the first trocar sheath into the patient's body cavity or lumen and which includes an elongated expandable tubular member which has leading and trailing portions, an impervious lining defining an inner lumen extending therein, an opening in the leading portion to facilitate insertion of the organ or other piece of tissue to be morcellated into the inner lumen and which is configured to pass though the first trocar sheath into a patient's body cavity or lumen, through at least a portion of the patient's body cavity or lumen and out of the patient's body cavity or lumen through the second trocar sheath.

2. The system of claim 1 wherein the impervious lining within the elongated expandable tubular member is formed by an elongated plastic tubular element which has outer transverse dimensions about the same as inner transverse dimensions of the elongated tubular member.

3. The system of claim 1 including means disposed within the inner lumen defined by the impervious lining of the elongated expandable tubular member to tear or cut fragments from an organ or piece of tissue disposed within the inner lumen.

4. The system of claim 3 wherein the means to cut or tear tissue fragments from the organ or piece of tissue is an elongated strip having a plurality of cutting elements thereon.

5. The system of claim 1 including a third trocar sheath configured to be inserted into the patient's internal body cavity and having an inner lumen in communication with the interior cavity to facilitate advancement into the internal cavity an endoscopic means to view the interior thereof.

6. An elongated tubular device for morcellating an organ or other piece of tissue within a patient's body cavity or lumen comprising:
    a) an elongated expandable outer tubular member which has leading and trailing portions, an impervious lining within the expandable outer tubular member having an interior defining an inner lumen extending therein and an opening in the leading portion to facilitate receiving the organ or other piece of tissue to be morcellated into the inner lumen and which is configured to pass though a first trocar sheath into a patient's body cavity or lumen, through at least a portion of the patient's body cavity or lumen and out of the patient's body cavity or lumen through a second trocar sheath; and b) means within the interior of the impervious lining for tearing or cutting fragments from the organ or other piece of tissue within the inner lumen.

7. The system of claim 6 wherein the means for tearing or cutting fragments from the piece of tissue includes at least one elongated strip which has a plurality of teeth thereon and which is secured within the interior of the impervious lining.

8. The elongated tubular device of claim 7 wherein the elongated strip is disposed within the impervious lining at a location proximal to the opening in the leading portion.

9. The elongated tubular device of claim 7 wherein the cutting elements comprise raised portions of the strip with sharp edges.

10. The elongated tubular device of claim 9 wherein the cutting elements are formed by forming a series of circular apertures in the strip and then pressing the trailing edge of the circular aperture outwardly from the strip.

11. The elongated tubular device of claim 7 wherein a plurality elongated strips having a plurality of cutting elements thereon are disposed within and secured to the interior of the impervious lining.

12. The system of claim 6 wherein the means for tearing or cutting fragments from the piece of tissue includes a helical ribbon having an exterior cutting surface which is secured to a supporting core.

13. The elongated tubular device of claim 6 wherein the impervious lining is formed of inelastic plastic material.

14. The elongated tubular device of claim 13 wherein the inelastic plastic material is a polymer of polyethylene.

15. A method for morcellating an organ or other piece of tissue within a patient's body cavity or lumen, comprising:

a) providing a morcellation means which includes:
an elongated expandable tubular member which has leading and trailing portions, an impervious lining disposed within the elongated expandable tubular member defining an inner lumen extending therein, an opening in the leading portion thereof to facilitate receiving the organ or other piece of tissue into the inner lumen defined by the impervious lining and which is configured to pass though a first trocar sheath into a patient's body cavity or lumen, through at least a portion of the patient's body cavity or lumen and out of the patient's body cavity or lumen through a second trocar sheath, and
means for tearing or cutting the organ or other piece of tissue which is disposed within the inner lumen defined by the impervious lining;

b) advancing the morcellation means into the patients's body cavity or lumen at one location, through a portion thereof and out of the patient's body cavity or lumen at another location;

c) disposing the organ or other piece of tissue within the inner lumen of the elongated expandable tubular member through the opening in the leading portion thereof:

d) tearing or cutting fragments from the organ or other piece of tissue disposed within the inner lumen; and e) withdrawing fragments from within the patient's body cavity or lumen by advancing the morcellation means out of the patient.

16. The method of claim 15 wherein the morcellation means is advanced into the patient's body cavity through an inner lumen of a first trocar sheath within the patient's body in fluid communication with the body cavity.

17. The method of claim 15 wherein the morcellation means is advanced out of the patient's body cavity through an inner lumen of a second trocar sheath within the patient's body in fluid communication with the body cavity.

18. The method of claim 15 wherein the tissue to be morcellated is the patient's kidney which is first severed from supporting tissue and then introduced into the inner lumen of the morcellation means through the opening in the leading section of the morcellation means.

19. An elongated member for morcellating an organ or other piece of tissue within a patient's body cavity or lumen, comprising:

a) an elongated expandable tubular member which has leading and trailing sections, a sealed interior and which is configured to pass though a first trocar sheath into a patient's body cavity or lumen, through at least a portion of the patient's body cavity or lumen and out of the patient's body cavity or lumen through a second trocar sheath, and;

b) an opening in the leading section which is configured to facilitate the introduction of the organ or other piece of tissue into the sealed interior; and c) means for tearing or cutting fragments of the organ or other piece of tissue disposed within the interior.

20. A kit for morcellating an organ or other piece of tissue within a patient's body cavity or lumen, comprising:

a) a morcellation means including;
an elongated expandable tubular member which has leading and trailing section, a sealed interior and which is configured to pass through a first trocar sheath into a patient's body cavity or lumen, through at least a portion of the patient's body cavity or lumen and out of the patient's body cavity or lumen through a second trocar sheath;
an opening in the leading section which is configured to facilitate the introduction of the organ or other piece of tissue into the sealed interior, and
means for tearing or cutting fragments of the organ or other piece of tissue disposed within the sealed interior; and b) a plurality of trocars which have sheaths with inner lumens configured to slidably receive the morcellation means.

21. An elongated member for removing an organ or tissue from within a patient's body cavity or lumen comprising an elongated expandable tubular member which has leading and trailing sections, a sealed interior, an opening in the leading section and which is configured to pass though a first trocar sheath into a patient's body cavity or lumen, through at least a portion of the patient's body cavity or lumen and out of the patient's body cavity or lumen through a second trocar sheath.

22. A method for removing an organ or other piece of tissue from within a patient's body cavity or lumen comprising:
   a) providing a tissue removing means which includes:
      an elongated expandable tubular member which has leading and trailing portions, an impervious lining disposed within the elongated expandable tubular member defining an inner lumen extending therein, an opening in the leading portion thereof to facilitate receiving the organ or other piece of tissue into the inner lumen defined by the impervious lining and which is configured to pass though a first trocar sheath into a patient's body cavity or lumen, through at least a portion of the patient's body cavity or lumen and out of the patient's body cavity or lumen through a second trocar sheath;
   b) advancing the tissue removing means into the patient's body cavity or lumen at one location, through a portion thereof and out of the patent's body cavity or lumen at another location;
   c) disposing the organ or other piece of tissue within the inner lumen of the elongated expandable tubular member through the opening in the leading portion thereof; and
   d) withdrawing the organ or other tissue fragments from within the patient's body cavity or lumen by advancing the tissue removal means out of the patient.

* * * * *